US009713569B2

(12) United States Patent
Nakamura

(10) Patent No.: US 9,713,569 B2
(45) Date of Patent: Jul. 25, 2017

(54) PRESSURIZED GAS MIST BATHING SYSTEM

(75) Inventor: Shoichi Nakamura, Nagano (JP)

(73) Assignees: ACP JAPAN CO., LTD., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 428 days.

(21) Appl. No.: 13/978,478

(22) PCT Filed: Feb. 17, 2012

(86) PCT No.: PCT/JP2012/053759

§ 371 (c)(1), (2), (4) Date: Jul. 5, 2013

(87) PCT Pub. No.: WO2012/111791

PCT Pub. Date: Aug. 23, 2012

(65) Prior Publication Data

US 2013/0281919 A1 Oct. 24, 2013

(30) Foreign Application Priority Data

Feb. 17, 2011 (JP) ................................ 2011-031831

(51) Int. Cl.

*A61M 35/00* (2006.01)
*A61H 33/02* (2006.01)

(Continued)

(52) U.S. Cl.

CPC ........... *A61H 33/028* (2013.01); *A61H 35/00* (2013.01); *A61H 33/02* (2013.01);

(Continued)

(58) Field of Classification Search

CPC .................. A61H 33/028; A61H 35/00; A61H 2201/0107; A61H 2201/0176;

(Continued)

(56) References Cited

U.S. PATENT DOCUMENTS 4,177,945 A * 12/1979 Schwartz ............ A61M 16/125 128/200.18
4,241,877 A * 12/1980 Hughes ..................... B05B 7/10 137/808

(Continued)

FOREIGN PATENT DOCUMENTS

GB 569753 A * 6/1945 ............ A61M 11/06
JP 2000-245841 A 12/2000
WO 2010/073754 A1 7/2010

*Primary Examiner* — Kathryn E Ditmer
(74) *Attorney, Agent, or Firm* — Manabu Kanesaka

(57) ABSTRACT

The invention is to provide a pressurized gas mist bathing system, ensuring hygiene and reduction in costs, by making only one part of the system disposable. This system causes a mist to contact the skin or the mucous membrane of a living body in a high pressure not less than a predetermined value, the mist is prepared by pulverizing liquid and the mist of micron size dissolving oxygen and/or carbon dioxide gases and comprises a gas supply means 10; a gas mist generating means 30 having a fluid nozzle 32 of generating the gas mist and a liquid storage 34 of storing liquid; a pressure cover 50 for covering the skin and the mucous membrane of the living body and formed with a space for sealing inside the gas mist supplied from the gas mist generating means 30; and a humors circulating means 41 for circulating the liquid from the liquid storage 34 of the gas mist generating means 30 to the fluid nozzle 32 and wherein, in the gas mist generating means 30, at least the liquid storage 34 is displaceable and replaced by another liquid storage.

20 Claims, 12 Drawing Sheets

(51) Int. Cl.
*A61H 35/00* (2006.01)
*A61H 33/14* (2006.01)

(52) U.S. Cl.
CPC .. *A61H 2033/143* (2013.01); *A61H 2033/145* (2013.01); *A61H 2201/0107* (2013.01); *A61H 2201/0176* (2013.01); *A61H 2201/105* (2013.01); *A61H 2201/164* (2013.01); *A61H 2201/1635* (2013.01); *A61H 2201/1652* (2013.01); *A61H 2201/5043* (2013.01); *A61H 2201/5071* (2013.01); *A61H 2201/5082* (2013.01); *A61H 2201/5089* (2013.01); *A61H 2205/06* (2013.01); *A61H 2205/10* (2013.01); *A61H 2205/12* (2013.01)

(58) Field of Classification Search
CPC .... A61H 2201/5082; A61H 2201/5089; A61H 2201/5071; A61H 2201/5043; A61H 2201/105; A61H 2201/164; A61H 2201/1635; A61H 2201/1652; A61H 33/14; A61H 2033/143; A61H 2033/145; A61M 11/00; A61M 11/02; A61M 11/06; A61M 16/10; A61M 16/108; A61M 16/1085; A61M 16/14; A61M 16/16; A61M 16/18; A61M 35/00; F24F 6/12; F24F 6/14; F24F 2006/143; B05B 7/00; B05B 7/0012; B05B 7/0075; B05B 7/04; B05B 7/0416; B05B 7/0433; B05B 7/0441; B05B 7/045; B05B 7/0458; B05B 7/0466; B05B 7/0475; B05B 7/0483; B05B 7/06; B05B 7/062; B05B 7/063; B05B 7/064; B05B 7/065; B05B 7/066; B05B 7/08; B05B 7/0807; B05B 7/0815; B05B 7/0869; B05B 7/16; B05B 7/24; B05B 7/2489; B05B 7/26; B05B 7/262; B05B 7/265; B05B 7/267; B05B 7/28; B05B 7/30; B05B 7/32
USPC .... 128/202.26, 202.12; 604/20, 22, 24, 290, 604/304, 308
See application file for complete search history.

(56) References Cited

U.S. PATENT DOCUMENTS

| | | | | |
|---|---|---|---|---|
| 4,461,425 | A * | 7/1984 | Miller | A61M 16/16 128/200.21 |
| 5,788,682 | A * | 8/1998 | Maget | 604/290 |
| 2008/0217262 | A1* | 9/2008 | Van Rijn | A61M 15/00 210/766 |
| 2009/0209877 | A1* | 8/2009 | Zhang | A61M 11/06 600/529 |
| 2010/0292659 | A1* | 11/2010 | Nakamura | A61H 33/14 604/289 |
| 2012/0065576 | A1* | 3/2012 | Stryker et al. | 604/20 |
| 2013/0079733 | A1* | 3/2013 | Burt et al. | 604/290 |

* cited by examiner

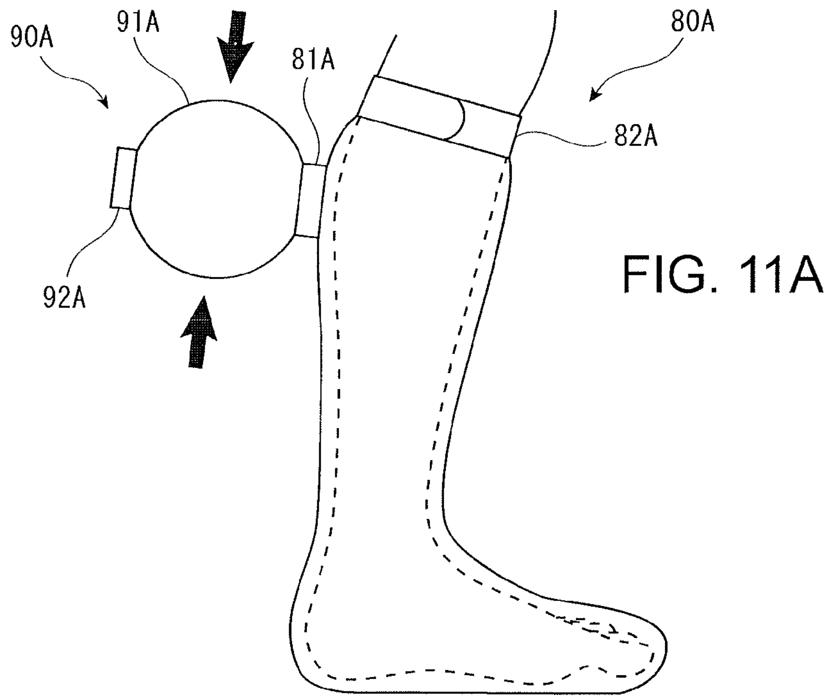
FIG. 11A
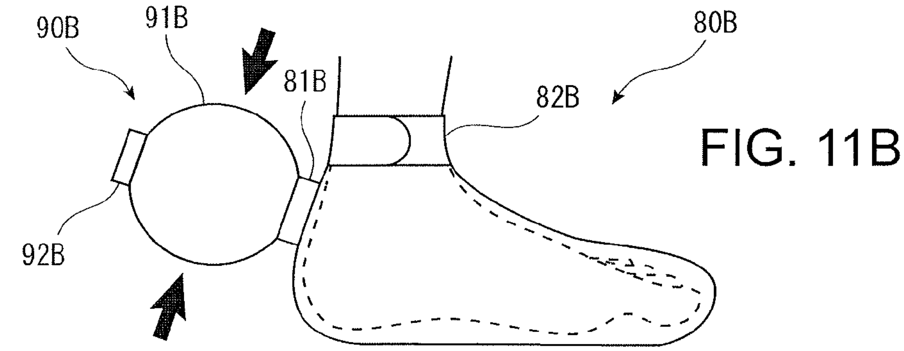
FIG. 11B
FIG. 11C
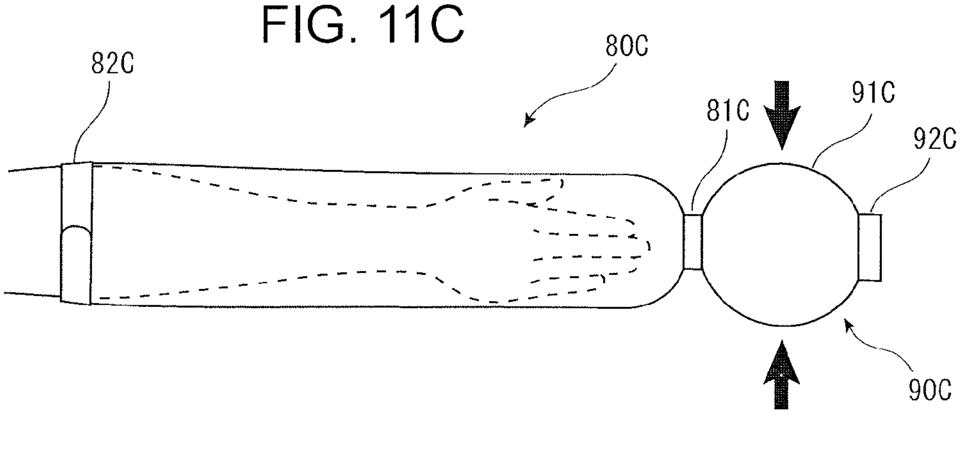

PRESSURIZED GAS MIST BATHING SYSTEM

RELATED APPLICATIONS

The present application is National Phase of International Application No. PCT/JP2012/053759 filed Feb. 17, 2012, and claims priority from Japanese Application No. 2011-031831, filed Feb. 17, 2011.

TECHNICAL FIELD

The present invention relates to a pressurized gas mist bathing system for improving absorption efficiency of gas into the skin or the mucous membrane of a living body, in which mist is prepared by pulverizing liquid including medicine and the mist of micron size dissolving oxygen and/or carbon dioxide gases, and the mist is caused to directly contact the skin or mucous membrane of the living body at pressure of not less than a predetermined value.

BACKGROUND OF THE INVENTION

Conventionally, it has been known that carbon dioxide (carbonic acid anhydride: $CO_2$) has two properties of being not only soluble in water (water-soluble) but also soluble in fat (fat-soluble) and, owing to having both properties, when only contacting to the skin and the mucous membrane of the living body which are like as mixed with water and fat, carbon dioxide penetrates under a subcutaneous tissue and expands blood vessels around the penetrated parts, and it works to improve the blood circulation. By this action of accelerating the blood circulation, it displays various physiological effects such as dropping of blood pressure, improving of metabolism or accelerating to remove pain substance or waste product. Further, it has also anti-inflammation and anti-bacterial function. Therefore, carbon dioxide has recently been given attentions also from viewpoints of improving health or beauty other than the purpose of medical cares.

In the tissue of the living body, carbon dioxide acts to release oxygen having been carried in combination with hemoglobin existing in a red blood cell. Around parts at the high concentration of carbon dioxide, the red blood cell releases more oxygen. Thus, supply of oxygen to cells by the red blood cell is mainly controlled by carbon dioxide. In short, being without carbon dioxide, hemoglobin remains as having been combined with oxygen and the cell becomes unable to receive oxygen. Carbon dioxide seems to be waste products resulted from action of the cell, however, as is seen, it plays in fact very important roles in the living body.

Further, recently, oxygen of the high concentration has also widely been known as effective over activity of metabolism, acceleration of blood circulation, fatigue recovery, or stability of blood pressure. Other than them, oxygen has effects of disinfection or sterilization by oxidation.

Thereupon, an inventor of this invention has developed a pressurized gas mist bathing device and system, in which a medicine is dissolved efficiently in oxygen or carbon dioxide, and in addition to these gases, a physiological action of the medicine is given effectively to the living body.

SUMMARY OF THE INVENTION

Problems that the Invention is to Solve

For ensuring hygiene of the pressurized gas mist bathing device as above mentioned, desirably a means of generating the gas mist is made disposable. However, a cost becomes higher for the disposable part and futility increases.

In view of the above mentioned circumstances, it is an object of the invention to provide such a pressurized gas mist bathing system, only one part of which is made disposable for ensuring hygiene so that reduction in costs can be realized.

Means for Solving the Problems

For solving the above mentioned problems, the invention is to provide a pressurized gas mist bathing system, which causes a mist to contact the skin or the mucous membrane of a living body, the mist (called as "gas mist" hereafter) having been prepared by pulverizing and dissolving carbon dioxide or oxygen and liquid, or a mixed gas (called as "gas" hereafter) of carbon dioxide and oxygen and liquid of concentration being not less than predetermined value, and which comprises a gas supply means; a gas mist generating means having a fluid nozzle of generating the gas mist and a liquid storage of storing liquid; a pressure cover for covering the skin and the mucous membrane of the living body and formed with a space for sealing inside the gas mist supplied from the gas mist generating means, and a humors circulating means for circulating the liquid from the liquid storage of the gas mist generating means to the fluid nozzle, wherein the gas mist generating means is characterized in that at least the liquid storage is displaceable and replaceable with another liquid storage.

By the way, the invention refers it as "pulverizing and dissolving" to pulverize the liquid into fine liquid drops, and cause to contact and mix with gas (carbon dioxide or oxygen, or the mixed gas of carbon dioxide and oxygen).

Herein, the pressurized gas mist bathing system of the invention is desirably further provided with sensors for detecting measured values of air pressure, temperature, concentration of oxygen and concentration of carbon dioxide, moisture and others, and control means for controlling an interior of the pressure cover based on the measured values of the sensors to be within ranges of the set values having been previously determined.

The humors circulating means is enough provided with a liquid pressurizing means.

Further on, it is also enough to equip a pressurizing means for pressurizing the interior of the pressure cover. By the way, this pressurizing means communicates with the pressure cover, and desirably consists of a hollow gas storage enabling to discharge the gas mist into the pressure cover.

If the gas mist is supplied intermittently into the pressure cover by the control means, the pressure cover may be effected with interval pressurization. Otherwise, if the pressurizing means intermittently discharges the gas mist into the pressure cover, it is also sufficient to carry out the interval pressurization on the pressure cover.

Next, it is preferable that the above mentioned liquid is any one or plural combination of water, ionic water, ozone water, physiological salt solution, purified water, or sterilized and purified water. And it is desirable to further contain any one or plural combination of menthol, vitamin E, vitamin C derivative, retinol, anesthetic agent, cyclodextrin, photo catalyst, complex of photo catalyst and apatite, hyaluronic acid, coenzyme Q10, seed oil, propolith, ethanol, chlorhexidine gluconate, amphoteric surface active agent, benzalkonium chloride, alkyl diamino etherglycine acetate, sodium hypo-chlorite, peracetic acid, sodium sesquicarbonate, silica, povidone-iodine, sodium hydrogen carbonate, carbonate spring agent of high concentration, anti-allergic agent, anti-inflammatory agent, anti-febrile agent, anti-fungus agent, anti-influenza virus agent, influenza vaccine, steroid agent, anti-cancer agent, anti-hypertensive agent, cosmetic, or trichogen.

A size of the mist supplied from the gas mist generating means into the pressure cover is suitably not larger than 10 μm.

The control means preferably holds pressure at 1.02 to 2.5 air pressure within the pressure cover when taking the pressurized gas mist bathing.

Further on, there may be provided an electric charge giving means for giving an electric charge to the mist supplied by the gas mist generating means. At this time, the electric charge is preferably minus.

Desirably, the gas mist generating means has a gas mist supply pipe for supplying the gas mist into the pressure cover, and this gas mist supply pipe is furnished with a filter for removing liquid drops attaching to the inside of the pipe. Still further, the gas mist supply pipe is suitably composed of a cornice shaped pipe over a whole or at one part of the gas mist supply pipe. In addition, this gas mist supply pipe is provided with a check valve.

The pressure cover is also desirably furnished with the check valve at the gas mist supply port.

By the way, it is suitable that the control means stops the gas supply from the gas supply means when the pressure value becomes more than the predetermined value.

The removable part of the gas mist generating means is in advance desirably sterilized.

In addition, the gas mist generating means is preferably provided with one or plural sheets of plates having inside fine pores for finely dividing the gas mists.

Effects of the Invention

According to the pressurized gas mist bathing system of the invention, by making replaceable the liquid storage in the gas mist generating means for enabling to replace with another liquid storage, it enables to pay attention to hygiene together with reduction in costs.

BRIEF DESCRIPTION OF THE DRAWINGS

FIGS. 11A-11C Typical views showing configuration examples (No. 1) of the pressure cover in the pressurized gas mist bathing system in dependence on the second embodiment of the invention;

EMBODIMENTS FOR PRACTICING THE INVENTION

In the following description, explanations will be made to embodiments of this invention, referring to the attached drawings.

First Embodiment

Figure 1:
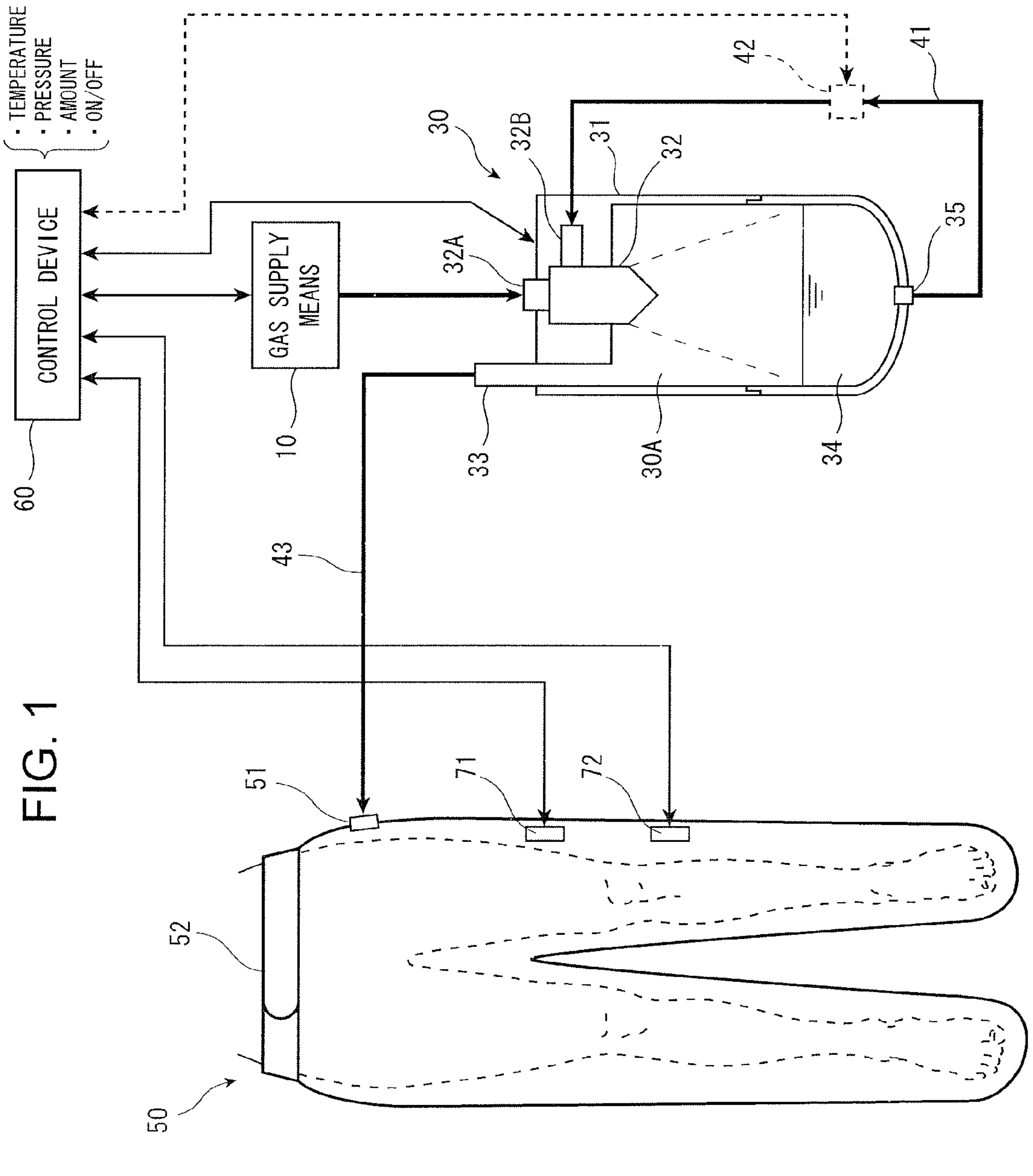
FIG. 1 A generally schematic view of the pressurized gas mist bathing system in dependence on the first embodiment of the invention.

FIG. 1 is the generally schematic view of the pressurized gas mist bathing system in dependence on the first embodiment of this invention. As shown in FIG. 1, the pressurized gas mist bathing system of the present embodiment comprises a gas supply means 10 for supplying oxygen, carbon dioxide, or the mixed gas (called briefly as "gas" hereafter) of oxygen and carbon dioxide, a gas mist generator 30 serving as a gas mist generating means, a liquid supply pipe 41 as a humors circulating means, a pressure cover 50 serving as a pressure cover means for sealing therein the supplied gas mist, and a control device 60 serving as a controlling means.

The gas supply means 10 is composed of a gas bomb and supplies gas to a fluid nozzle 32 of a later mentioned gas mist generator 30. The gas supply means 10 is provided with a regulator for adjusting pressure of gas, though not illustrated. There may be equipped a heater and a temperature gauge for controlling gas temperature.

The gas mist generator 30 stores the liquid therein, generates the gas mist made by pulverizing and dissolving the liquid and gas by high speed flow of gas supplied from the gas supply means 10, and supplies this gas mist into the pressure cover 50. As shown in FIG. 1, the gas mist generator 30 is composed with a generator main body 31 and a liquid storage 34 which is removable from this generator main body 31.

The generator main body 31 is a part of composing the upper half of the gas mist generator 30, and on an upper part of an almost cylindrical container opening its lower portion, there are provided the fluid nozzle 32 for generating the gas mist and a gas mist outlet 33 for discharging the gas mist.

The fluid nozzle 32 is a binary nozzle which generates the gas mist by utilizing high speed of gas supplied from the gas supply means 10. The fluid nozzle 32 has a gas supply part 32A connected with the gas supply means 10 and a liquid supply part 32B connected with a later mentioned liquid outlet 35. The gas mist generated by the fluid nozzle 32 is discharged into a space 30A defined inside when setting the generator main body 31 and the liquid storage 34, and this gas mist is expelled from a gas mist outlet 33. A size of the mist then generated is desirably fine, and concretely being not larger than 10 μm is optimum. Thus finely pulverized mist can display an effect of minus ion.

Figure 2:
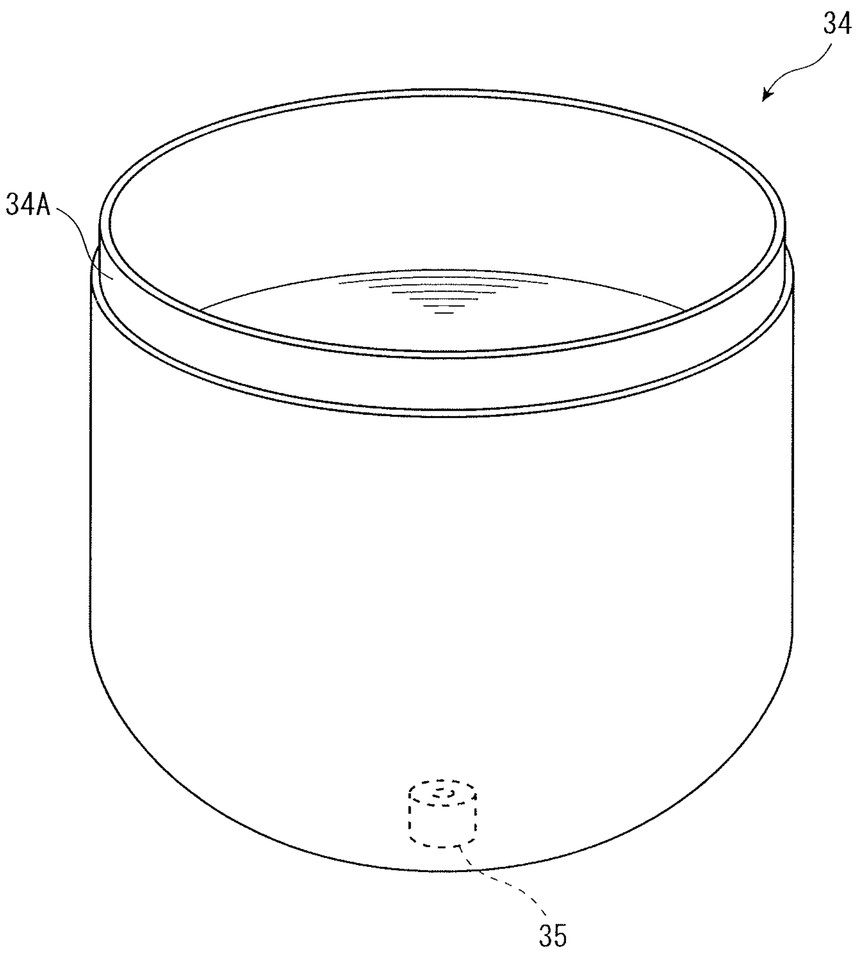
FIG. 2 A perspective view showing an outline of a liquid storage in the pressurized gas mist bathing system of FIG. 1.

The liquid storage 34 is a part composing the lower half of the gas mist generator 30, and this is a container shaped as a funnel at a bottom as shown in FIG. 2. The liquid storage 34 is furnished at its upper part with a connecting part 34A, and by means of this connecting part 34A, the generator main body 31 is connected at its lower part. The liquid storage 34 has a liquid outlet 35 at its lower part for discharging the inside liquid to the fluid nozzle 32.

Figure 3A:
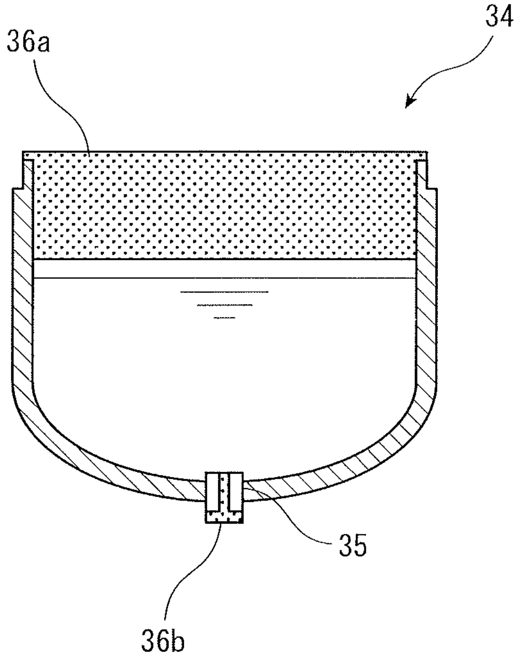
FIGS. 3A-3B Typical views showing embodiments of sealing the liquid storage in the pressurized gas mist bathing system of FIG. 1.
Figure 3B:
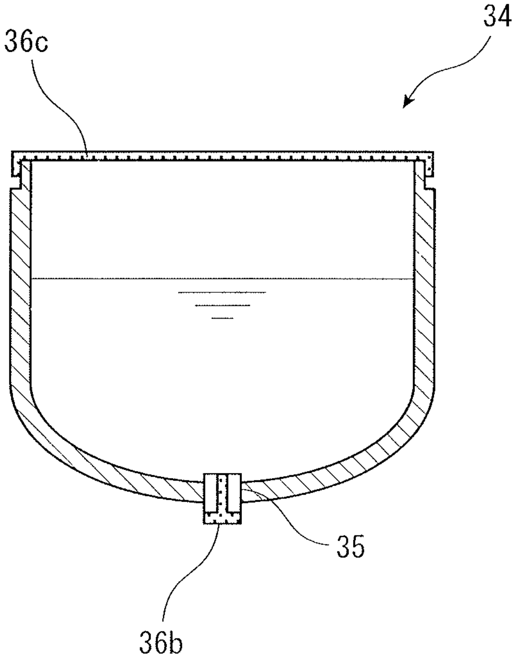

The liquid storage 34 has been in advance stored with a predetermined liquid when having built at a stage of setting up the system of this invention, and the connecting part 34A and the liquid outlet 35 are sealed. FIGS. 3A-3B are the typical views showing the embodiments of sealing the liquid storage 34. FIG. 3A shows an example of sealing the liquid storage 34 at its upper and lower parts with plugs 36*a*, 36*b* made of elastic members such as rubbers. FIG. 3B shows an example of sealing the liquid storage 34 at its upper part with a film 36*c* made of an aluminum or a plastic by heating or with an adhesive, and sealing the lower part with a plug 36*b* made of an elastic member as a rubber. When using the gas mist generator 30, the liquid storage 34 sealed as above mentioned is opened and set on the generator main body 31, and after having used, preferably the liquid storage 34 and all are disused.

Thus, in this invention, the liquid storage 34 of the gas mist generator 30 is made attachable and detachable, and after having used, it can be discarded. That is, by making the at least liquid storage 34 removable and replaceable with another new liquid storage 34, it is possible to keep hygienic and to realize cost reduction. In particular, since the liquid storage 34 is simple in the structure, too, a restraining effect of cost is high in comparison with a case of making the whole of the gas mist generator 30 replaceable. Further on, since the liquid can be previously stored in the replaceable part, it is possible to save a structure of supplying a liquid such as a medicine, and it is possible to realize reduction in size and in cost. By the way, this replaceable liquid storage 34 is preferably sterilized in a manufacturing stage. In addition, non-replaceable and remaining parts of the gas mist generator 30 are also dealt with sterilization treatment prior to use.

Herein, for the liquid stored in the liquid storage 34, it is preferable to employ water, ionic water, ozone water physiological salt solution, purified water or sterilized and purified water. Further, these liquids are sufficient to contain medicines useful to users' diseases or symptom. As the medicines, for example, listed are anti-allergic agent, anti-inflammatory agent, anti-febrile agent, anti-fungus agent, anti-influenza virus agent, influenza vaccine, steroid agent, anti-cancer agent, anti-hypertensive agent, cosmetic, or trichogen. Further, these liquids are further possible to generate synergistic effects by coupling with a gas physiological action with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic agent moderating irritation to the mucous membrane; cyclodextrin removing odor; photocatalysis or a complex of photocatalysis and apatite having disinfection and anti-phlogistic; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, ant-inflammatory agent, pain-killing, anesthetic, and immunity. Otherwise, the liquid may be added with ethanol, gluconic acid chlorohexizine, amphoteric surface active agent, benzalkonium chloride, alkyldiamino ether glycin acetate, sodium hypochlorite, acetyl hydroperoxide, sodium sesqui-carbonate, silica, povidone-iodine, sodium hydrogen carbonate. In addition, carbonate spring of high concentration may be added (examples of organic components are sulfate, carbonate, or sodium dichloroiso-cyanurate).

Under a condition of holding the liquid as mentioned above, when setting the liquid storage 34 in the generator main body 31 and supplying gas from the gas supply means 10 into the fluid nozzle 32, the interior of the gas mist generator 30 becomes high pressure and the liquid is sent from the liquid outlet 35 into the liquid supply pipe 41. The liquid reaching from the liquid supply pipe 41 to the liquid supply part 32B of the fluid nozzle 32 is changed into a gas mist by the fluid nozzle 32, and sprayed to the space 30A. The gas mist filled in the space 30A is almost supplied into the pressure cover 50 via the gas mist supply pipe 43 from the gas mist outlet 33, while one part of the gas mist melts into the liquid stored in the liquid storage 34. By melting into the gas mist, this liquid is dissolved with the gas and is further sent into the liquid supply pipe 41, this liquid is sprayed as the gas mist from the fluid nozzle 32, and such actuations are repeated. As a result, while the liquid stored in the liquid storage 34 circulates, a dissolving concentration of the gas becomes gradually higher, and it becomes possible to generate the gas mist much dissolved with the gas.

By the way, for efficiently circulating the liquid in the liquid supply pipe 41, it is sufficient to arrange a liquid pressurizer 42 such as a pump to the liquid supply pipe 41.

Figure 4:
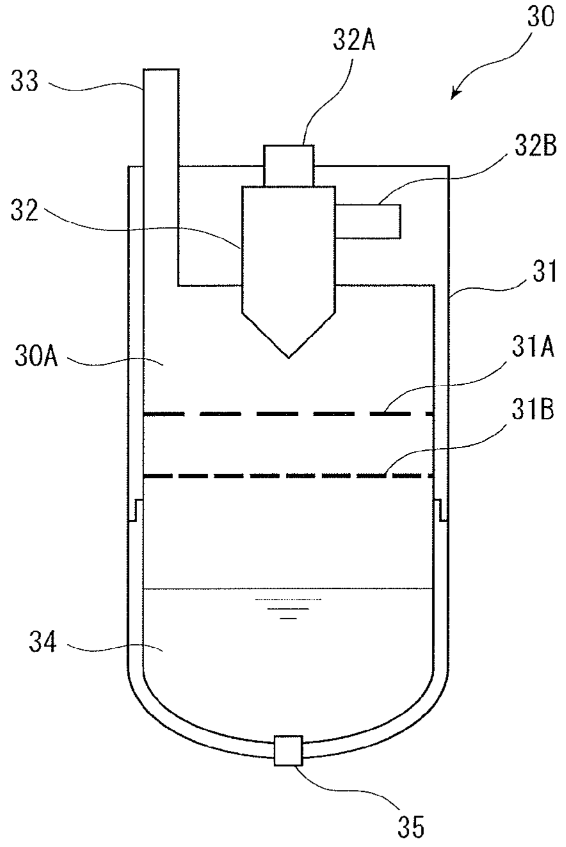
FIG. 4 A typical view showing an example of placing plates to the gas mist generator of the invention.
Figure 5A:
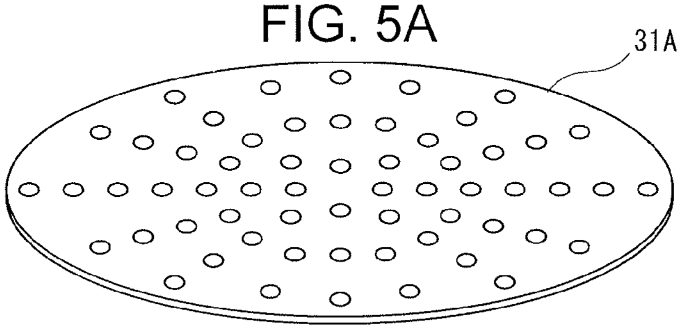
FIGS. 5A-5B Perspective views showing concrete examples of the plates of FIG. 4.
Figure 5B:
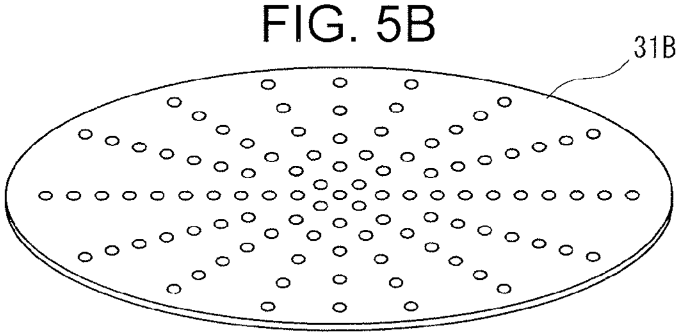

It is enough to provide one or plural sheets (herein, two sheets, as an example) of plates 31A, 31B above the surface of the stored liquid for refining the generated gas mist in the space 30A of the interior of the gas mist generator 30 as shown in FIG. 4. FIGS. 5A-5B show examples of the plates 31A, 31B. Thus, the plates 31A, 31B are formed with plural pores respectively, and the generated gas mist is refined by passing through these pores. With respect to the plate 31A being nearer to the fluid nozzle 32 and the farther plate 31B, the diameters of the pores of the nearer plate 31A are made larger than those of the pores of the lower plate 31B.

Figure 6:
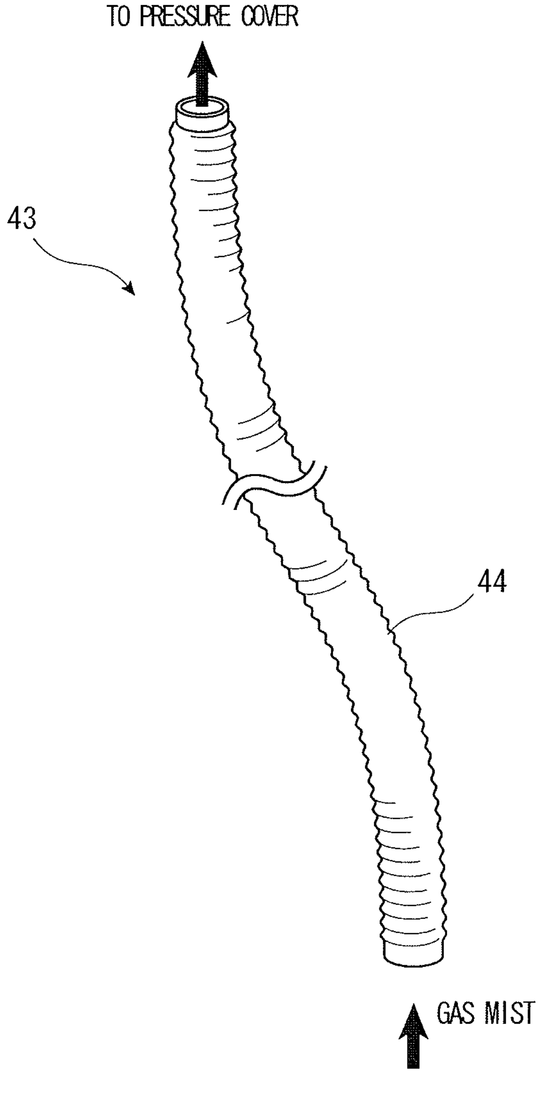
FIG. 6 A typical view showing an example of connecting the gas mist generator and the pressure cover of the invention.

The gas mist generated by the gas mist generator 30 is supplied to the pressure cover 50 from the gas mist outlet 33 via the gas mist supply pipe 43. The gas mist supply pipe 43 is furnished inside with a check valve for preventing back flow of the gas mist. Also in the gas mist supply pipe 43, though not illustrated, it is enough to furnish a droplet-removing filter for removing surplus liquid drops attached to the inside of the pipe. Preferably, the gas mist supply pipe 43 is composed wholly or partially with a soft pipe 44 formed into a bellows shape and having a large diameter as shown in FIG. 6. If composing the gas mist supply pipe 43 with the cornice shaped pipe 44, it is freely bent and contracted so that the user's action is not limited. In addition, even if the gas mist flowing in the gas mist supply pipe 43 becomes gradually liquefied, the cornice can remove the liquid owing to its concave and convex parts.

The pressure cover 50 enables to form a space for covering the skin and mucous membrane of the living body (herein, as the example, the lower extremity of the living body) and to seal the gas mist inside. As an example, FIG. 1 shows a shape as trousers covering the lower extremity of the living body. The pressure cover 50 is composed of a pressure resistant, non-air permeable and non-moisture permeable material, for example, preferably, the natural rubber, silicone rubber, polyethylene, polypropylene, polyvinylidene chloride, poly-stylene, polyvinyl acetate, polyvinyl chloride, polyamide resin, poly-tetrafluoroethylene.

The pressure cover 50 is connected to the gas mist supply pipe 43 and has the supply port 51 for introducing the gas mist inside. The supply port 51 is provided inside with the check valve to prevent from back-flow of the gas mist. The pressure cover 50 may have an open or a valve enabling to exhaust the gas mist for controlling inside pressure. Pressure control may be performed manually, but is desirably automatically based on measuring values of a later mentioned manometer 71 by a control device 60 together with supply or control of the gas mist. Further, a safety valve (by-pass valve) may be provided for automatically opening the valve when the inside of the pressure cover 50 becomes more than a constant pressure.

The pressure cover 50 is inside installed with a manometer 71 for measuring internal pressure. The control device 60 controls generation or supply of the gas mist on the basis of measuring values of the manometer 71 for maintaining a pressure value within the pressure cover 50 to be more than 1 air pressure (more preferably, around 1.02 to 2.5 air pressure). For example, supply of gas from the gas supply means 10 is controlled or stopped, otherwise, the gas mist from the pressure cover 50 is exhausted. Further, the pressure cover 50 is inside installed with a temperature gauge 72 for measuring temperature within the pressure cover 50. The control device 60 performs "on-off" of a heater installed in the gas supply means 10 on the basis of measuring values of the temperature gauge 72 for maintaining a determined temperature (for example, around 38° C.) bringing about warm bath effects within the pressure cover 50. As to others, the pressure cover 50 may be installed inside with sensors for measuring concentrations of oxygen and carbon dioxide, moisture and others for controlling interiors of the cover based on the measured values to be within ranges of predetermined values by the control 60.

The pressure cover 50 has, around its opening, a stopper 52 for attaching to and detaching from the living body (herein, the lower extremity of the living body) and for preventing leakage of the gas mist. The stopper 52 is suitably composed of, e.g., a face fastener of stretching property, or may have a sole string, rubber or their combination. For heightening a sealing property of the pressure cover 50, the inside (such as an inside of the stopper 52) thereof may have a material attaching to the user's skin. The adhesive material is preferably, for example, a visco-elastic gel made of poly-urethane or silicone rubber. Further this adhesive material is detachably used and exchangeable each time or if viscosity becomes weak.

The control device 60 is composed of a computer having CPU, memory and display. Pressure control, on-off switch of gas supplied from the gas supply means 10 or on-off switch of supply of the gas mist are performed for taking the pressurized gas mist bathing under the optimum condition. In particular, such a structure is desirable that, when the pressure value becomes more than a predetermined value in the pressure cover 50, the structure stops supplying the gas from the gas supply means 10 by the control device 60.

Next, reference will be made to one example of sequences taking the gas mist bathing by use of the pressurized gas mist bathing system of the above mentioned first embodiment.

At first, the sealed liquid storage 34 is opened, the generator main body 31 and the liquid supply pipe 41 are set to complete the gas mist generator 30. The pressure cover 50 is fixedly secured to the living body (herein, the lower extremity of the living body) and closed.

Subsequently, gas supply from the gas supply means 10 to the gas mist generator 30 starts. When the gas is supplied in the fluid nozzle 32, the gas is discharged from the fluid nozzle 32 into the space 30A in the gas mist generator 30. Then, the inside of the gas mist generator 30 becomes high pressure, and the liquid in the liquid storage 34 is sent to a liquid supply part 32B of the fluid nozzle 32 via the liquid supply pipe 41. When the gas and the liquid are supplied in the fluid nozzle 32, generation of the gas mist starts, and the generated gas mist spreads in the space 30A, and the gas mist is supplied into the pressure cover 50 from the gas mist outlet 33 via the gas mist supply pipe 43. During generation of the gas mist, the control device 60 adjusts supplying pressure or temperature of the gas.

The generated gas mist passes the gas mist supply pipe 43 and is provided into the pressure cover 50 from a supply port 51. The control device 60 adjusts each of the means from the measuring values of a manometer 71 and a temperature gauge 72 placed in the pressure cover 50, such that the inside of the pressure cover 50 is made optimum pressurized and heated condition (around 1.02 to 2.5 air pressure and around 38° C.), and under these conditions, the pressurized gas mist bathing is performed.

The above mentioned explanation has been made to the lower extremities of the human living body as the example to be performed with the pressurized gas mist bathing, and the invention is applicable to various parts of the living body. Then, the optimum pressurized gas mist bathing is performed by using the shapes of the pressure cover 50 meeting objective parts of the living body.

Figure 7:
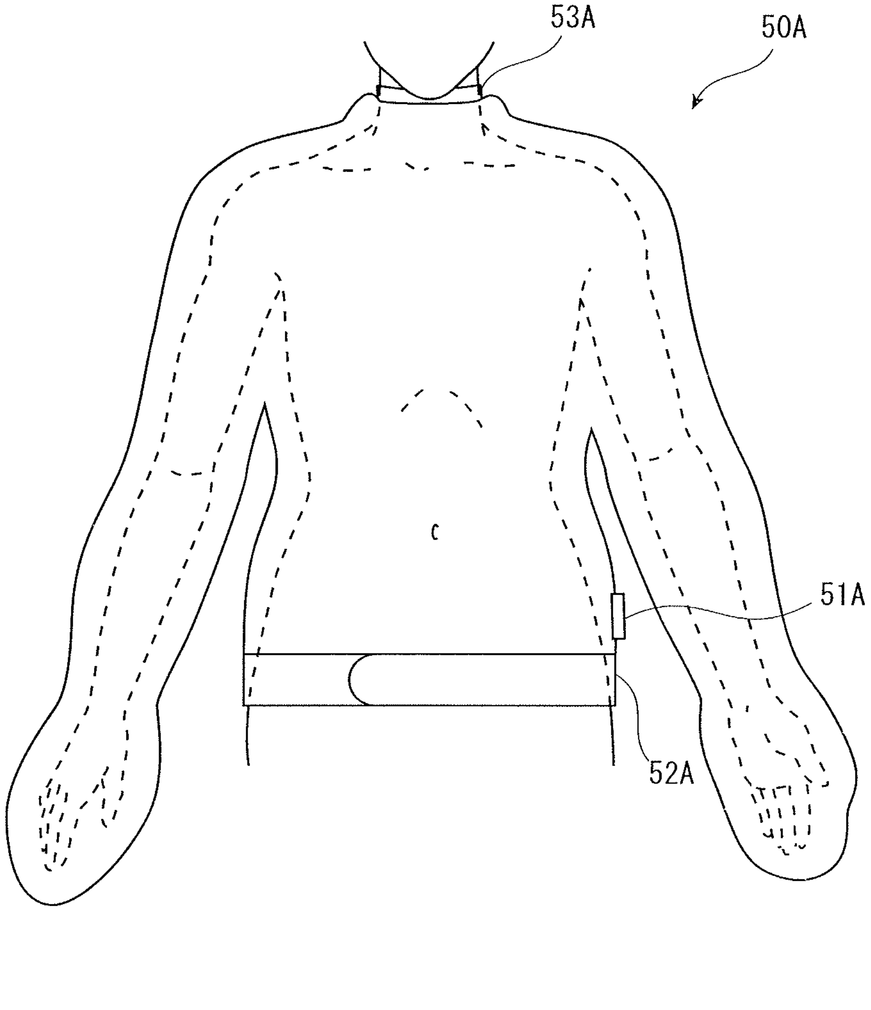
FIG. 7 A typical view showing a configuration example (No. 1) of the pressure cover in the pressurized gas mist bathing system in dependence on the first embodiment of the invention.

FIGS. 7 to 9A-9B show the various shaped examples of the pressure cover 50. At first, FIG. 7 shows the schematic view of the pressure cover 50A for the upper half of the living body. The pressure cover 50A has a shape for wrapping the whole of the upper half of the living body, and has a stopper 52A for attaching to and detaching from the living body when opening a waist part and stopping leakage of the gas mist sealed inside. A stopper 53A is similarly formed around the opening of a neck. 51A designates a supply port for introducing the gas mist inside of the pressure cover 50A.

Figure 8A:
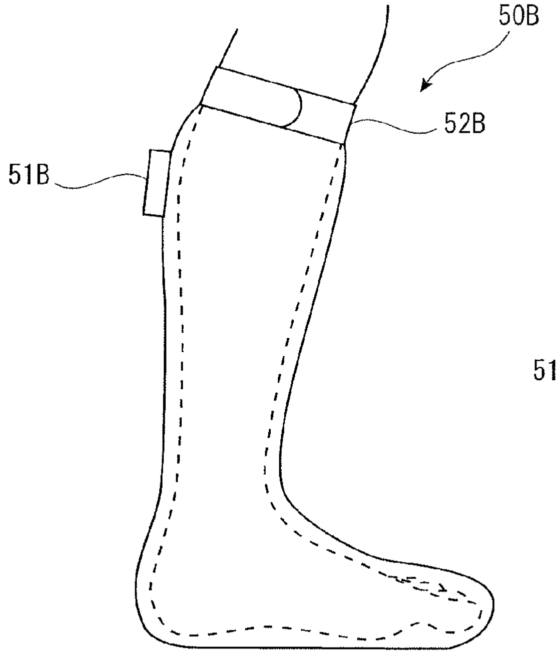
FIGS. 8A-8D Typical views showing configuration examples (No. 2) of the pressure cover in the pressurized gas mist bathing system in dependence on the first embodiment of the invention.
Figure 8B:
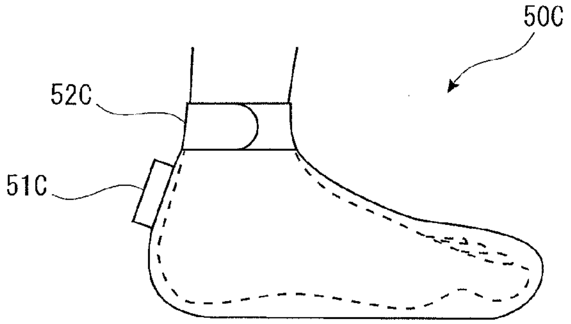
Figure 8C:
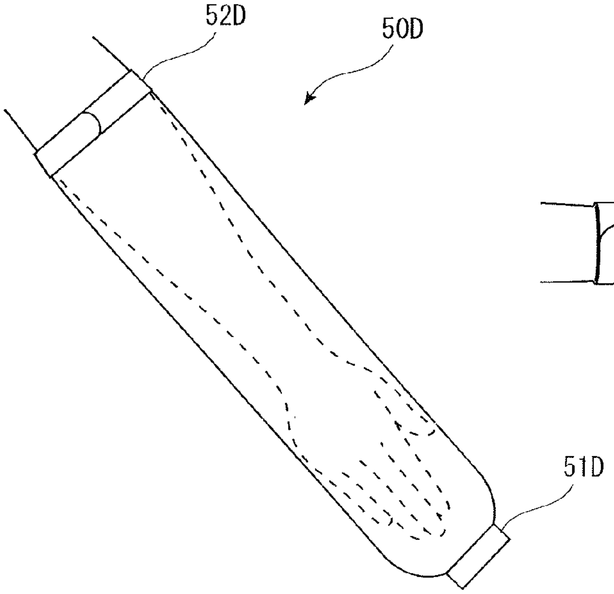
Figure 8D:
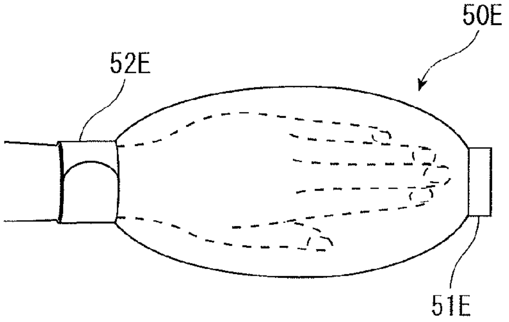

FIGS. 8A-8D show the variously shaped examples of the pressure cover 50 for covering further limited parts of the living body. FIG. 8A is a pressure cover 50B for one-side lower extremity (lower part under a knee) of the living body. The pressure cover 50B has a stopper 52B at its opening part and a supply port 51B for introducing inside the gas mist. FIG. 8B is a pressure cover 50C for a foot. The pressure cover 50C has a stopper 52C at its opening part and a supply port 51C for introducing inside the gas mist. FIG. 8C is a pressure cover 50D for a forearm. The pressure cover 50D has a stopper 52D at its opening part and a supply port 51D for introducing inside the gas mist. FIG. 8D is a pressure cover 50E for a hand. The pressure cover 50E has a stopper 52E at its opening part and a supply port 51E for introducing the gas mist inside thereof.

Figure 9A:
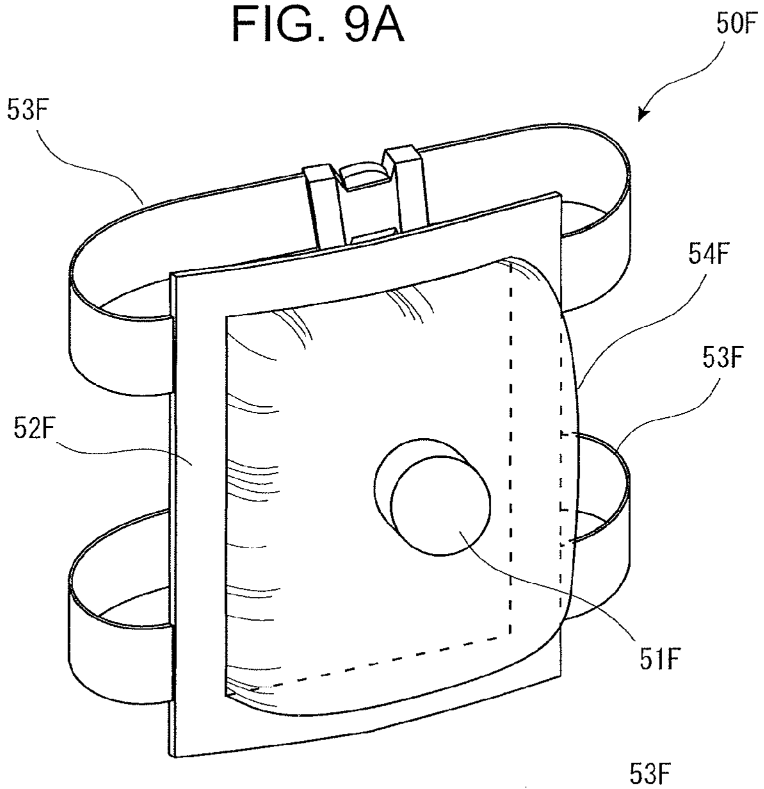
FIGS. 9A-9B Typical views showing a configuration example (No. 3) of the pressure cover in the pressurized gas mist bathing system in dependence on the first embodiment of the invention.
Figure 9B:
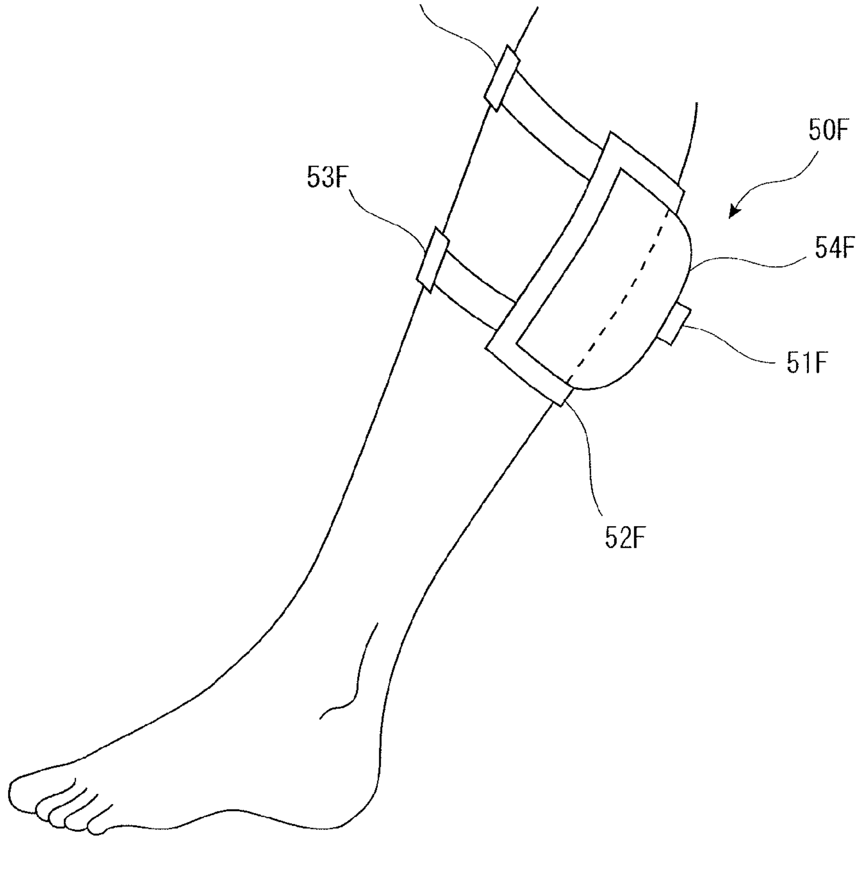

FIGS. 9A-9B show examples of a patch shaped pressure cover 50F. FIG. 9A is a view showing the outline of the patch shaped pressure cover 50F. FIG. 9B is a view showing an external appearance when attaching the patch shaped pressure cover 50F to the living body (herein, the lower extremity). The pressure cover 50F is composed of a cover part 54F for covering the skin and mucous membrane of the living body, a stopper 52F provided at the margin of the cover part 54F and directly attached to the skin and mucous membrane, fasteners 53F made of belts or strings for fastening the cover part 545 to the living body, and a supply port 51F for supplying the gas mist into the space defined by the cover 54F and the stopper 52F.

In regard to the pressure cover 50, various shapes may be assumed other than the examples shown in FIGS. 7 to 9A-9B. In particular, since this invention can be applied to not only the human living body, but also to general kinds of animals, the pressure cover 50 adopts shapes in view of the using objects and using parts. In sum, if enabling to form spaces for sealing the skins and the mucous membranes of the living body and to form inside spaces for sealing the gas mist, any shapes are sufficient. Although omitting illustrations here, it is suitable to furnish air ports for discharging the gas mist in the pressure cover 50 or controlling pressurization.

The pressurized gas mist bathing contacts the gas mist to the skin and mucous membrane of the living body at pressure of more than the predetermined value, and such pressurization heightens the effects by performing as pulsing at predetermined intervals, and therefore it is sufficient that the control device 60 supplies the gas mist into the pressure cover 50 intermittently at fixed rhythm. As to the interval pressurization at such a case, if synchronizing with pulsations, the effects are more heightened.

Second Embodiment

Figure 10:
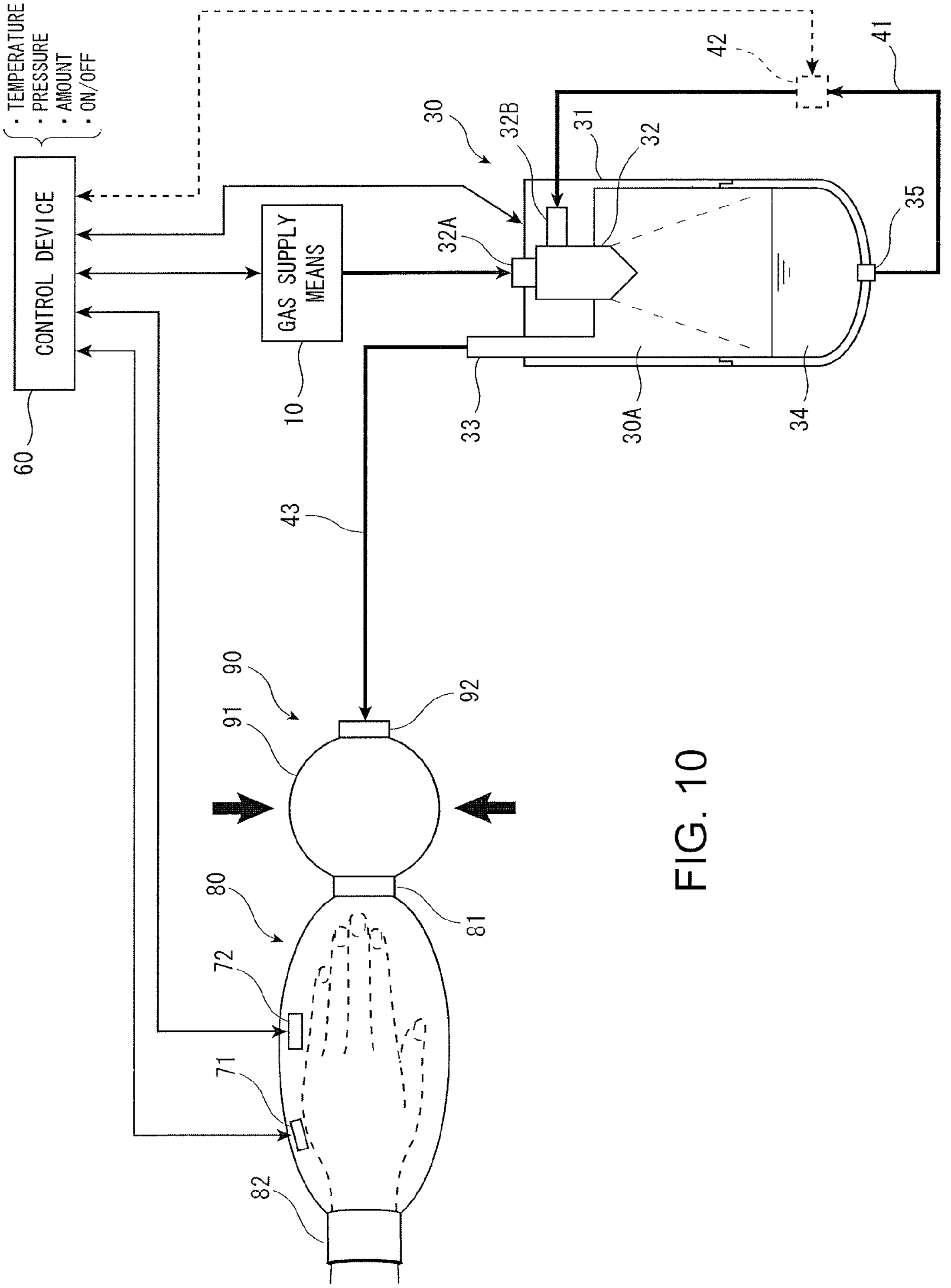
FIG. 10 A generally schematic view of the pressurized gas mist bathing system in dependence on a second embodiment of the invention.

FIG. 10 is the generally schematic view of the pressurized gas mist bathing system in dependence on a second embodiment of this invention. This embodiment will explain the pressurized gas mist bathing system further having a pressurizing means for simplifying pressurization within the pressure cover. As to the same parts as those of the first embodiment shown in FIG. 1, the same numerals will be given, and detailed explanation will be omitted.

As shown in FIG. 10, the pressurized gas mist bathing system of this embodiment has a pressure cover 80 forming a space into which the gas mist is sealed and a pressurizing means 90 connecting the pressure cover 80 for carrying out pressurization therein.

The pressure cover 80 has almost the same structure of the pressure cover 50 shown in the first embodiment, and has a gas mist supply port 81 and a stopper 82, providing in the present embodiment that the supply port 81 is connected to the pressurizing means 90. By the way, as an example herein, the pressure cover 80 having a shape of covering a hand of the living body is illustrated.

The pressurizing means 90 pressurizes the inside of the pressure cover 80, and therefore has a hollow gas storage 91 communicating with the pressure cover 80. The gas storage 91 is composed of a soft material having pressure resistance, non-air permeability and non-moisture permeability. The pressurizing means 90 is connected to the supply port 81 of the pressure cover 80, and has a supply port 92, from which the gas mist is supplied into the gas storage 91. In addition, the supply port 92 of the pressurizing means 90 is also provided inside with the check valve for checking back-flow of the gas mist.

For pressurizing the pressure cover 80 by the pressurizing means 90, the gas mist is stored in the gas storage 91 under a condition where the moderate gas mist is stored within the pressure cover 80. If pressurizing the gas storage 91 in a manner as crashing as shown with arrows in FIG. 10, the gas mist in the gas storage 91 is exhausted into the pressure cover 80, so that the inside of the pressure cover 80 can be pressurized.

The pressurizing means 90 is enough with a structure of manually pushing, or sufficient to mechanically control by the control device 60 using a driving device. As mentioned above, since pressurization in the pressurized gas mist bath heightens effects by pulse-like performance of a determined interval, it is effective to intermittently push the pressurizing means 90 at constant rhythm.

When taking the pressurized gas mist bathing by use of the pressurized gas mist bathing system of this embodiment, at first, the sealed liquid storage 34 is opened, the generator main body 31 and the liquid supply pipe 41 are set, so that the gas mist generator 30 is accomplished. The pressure cover 80 is fixed to the living body (herein, the hand) and connected to the pressurizing means 90 and closed.

Supply of gas starts from the gas supply means 10 into the gas mist generator 30 for generating the gas mist. During this period, the control device 60 controls supply pressure of gas, temperature and others.

The generated gas mist is discharged from the gas mist outlet 33 into the pressurizing means 90 and the pressure cover 80 through gas mist supply pipe 43. The control device 60 makes adjustments from measuring values of the temperature gauge 72 placed within the pressure cover 80, such that the inside of the pressure cover 80 is maintained under the optimum heated condition (for example, around 38° C.). When the gas mist of the optimum amount is stored in the pressure cover 80 and the pressurizing means 90, the pressurizing means 90 is pushed to moderately pressurize (around 1.02 to 2.5 air pressure) the pressure cover 80 for taking the gas mist pressurizing bathing.

As having mentioned in the first embodiment, various shapes of the pressure cover 80 may be employed, since they are applied to many parts of the living body, providing that, in the present embodiment, the pressure cover 80 must have a size easily pressurized by the pressuring means 90. For example, when manually pressurizing the pressuring means 90, the pressuring means 90 must have such a size grasped by man's one or both hands, and the pressure cover 80 pressurized with the pressuring means 90 is also limited to in a certain size, accordingly. Further, even if, in a case of pressurizing with such as a driving device, the pressuring means 90 as well as a means pressurizing this means 90 are desirably compact not to actually keep wide places, therefore, the present embodiment is applicable to the pressure cover 80 which is comparatively compact (covering local parts of the living body).

FIGS. 11A-11C and 12A-12B show the examples of shapes of the pressure cover 80 to which the present embodiment is easily applied as well as those of the pressuring means 90 connected thereto. FIG. 11A is a pressure cover 80A for one-side lower extremity (lower part under a knee) of the living body. The pressure cover 80A has a supply port 81A for introducing inside the gas mist, and the stopper 82A at its open. The supply port 81A is connected to a pressuring means 90A. The pressuring means 90A has a gas storage 91A and a supply port 92A. FIG. 11B is a pressure cover 80B for foot. The pressure cover 80B has a supply port 81B for introducing inside the gas mist and a stopper 82B at its opening part. A stopper 82B is provided at its opening part. The supply port 81B is connected with a pressurizing means 90B. The pressurizing means 90B has a gas storage 91B and a supply port 92B. FIG. 11C is a pressure cover 80C for a forearm. The pressure cover 80C has a supply port 81C for introducing inside the gas mist and a stopper 82C at its opening part. The supply port 81C is connected with a pressurizing means 90C. The pressurizing means 90C has a gas storage 91C and a supply port 92C.

Figure 12A:
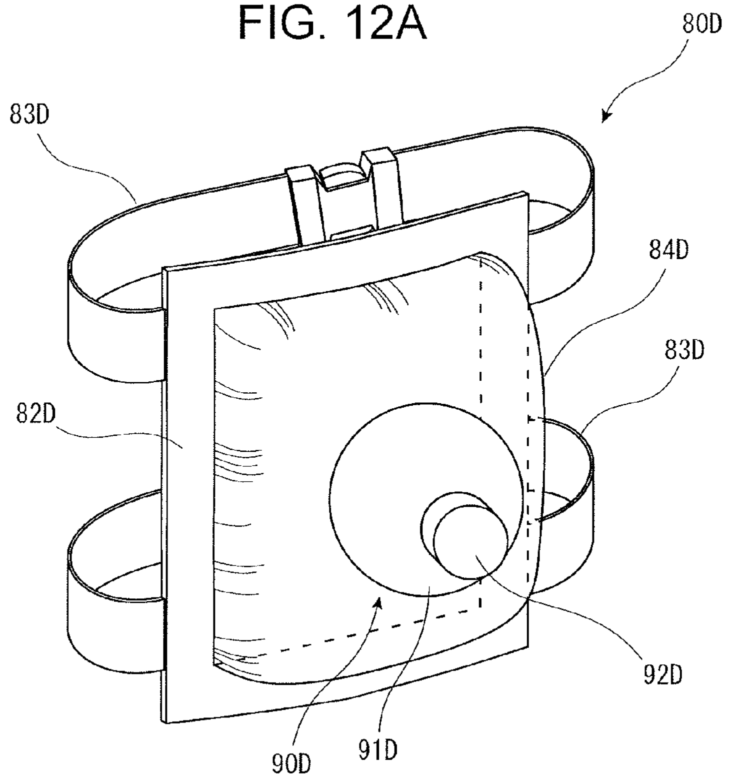
FIGS. 12A-12B Typical views showing a configuration example (No. 2) of the pressure cover in the pressurized gas mist bathing system in dependence on the second embodiment of the invention.
Figure 12B:
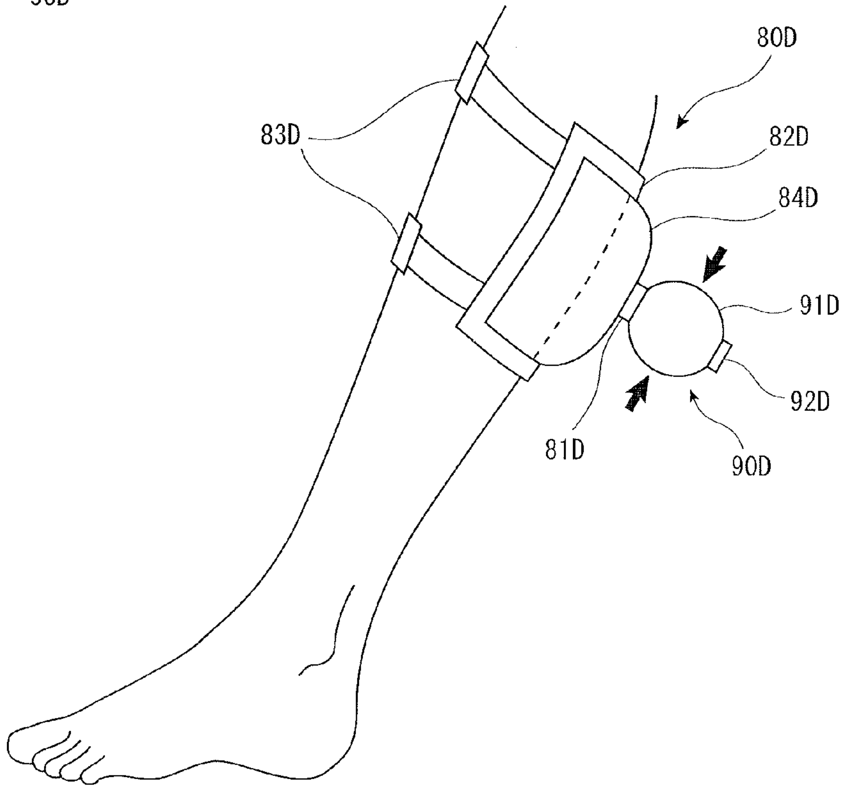

FIGS. 12A-12B show a patch shaped pressure cover 80D. FIG. 12A is a view showing the outline of the patch shaped pressure cover 80D. FIG. 12B is a view showing an external appearance when attaching the patch shaped pressure cover 80D to the living body (here, the lower extremity). The pressure cover 80D is composed of a cover part 84D for covering the skin and mucous membrane of the living body, a stopper 82D provided at the margin of the cover part 84D and directly attached to the skin and mucous membrane of the living body, fasteners 83D made of belts or strings for fastening the cover part 84D to the living body, and a supply port 81D for supplying the gas mist into the space defined by the cover 84D and the stopper 82D. The supply port 81D is connected with the pressurizing means 90D. The pressurizing means 90D has the gas storage 91D and the supply port 92D.

Incidentally, although having not shown here, preferably there is provided an exhaust port for exhausting the gas mist in the pressure cover 80 or adjusting pressure.

In the above embodiment, the pressurizing means 90 is composed of a hollow gas storage 91 communicating to the pressure cover 80, and any members are sufficient if enabling to conveniently pressurize the pressure cover 80 such as a member compressing to crash the pressure cover 80 from an outer periphery.

Third Embodiment

Figure 13:
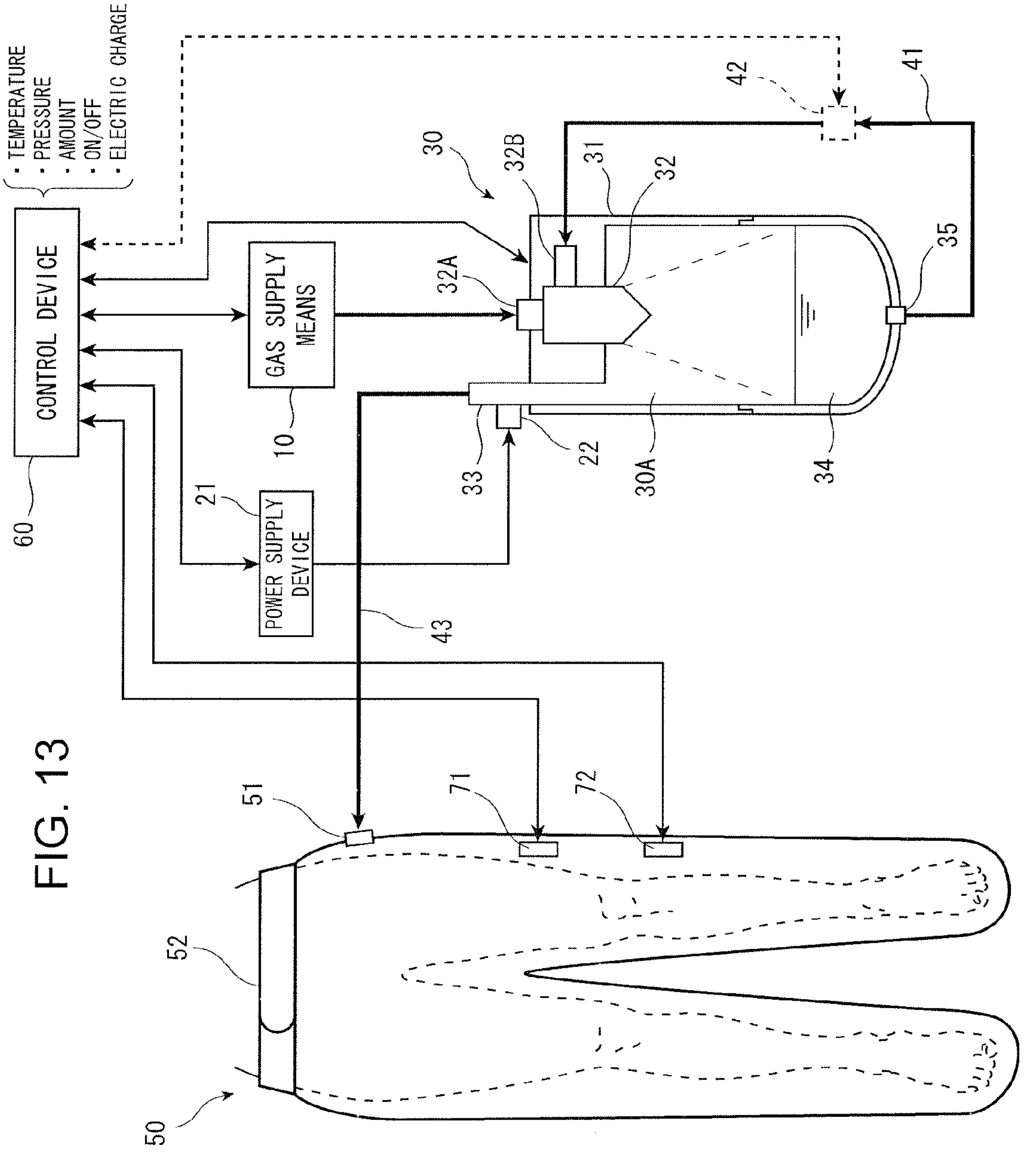
FIG. 13 A generally schematic view of the pressurized gas mist bathing system in dependence on a third embodiment of the invention.

FIG. 13 is the generally schematic view of the pressurized gas mist bathing system in dependence on a third embodiment of this invention. This embodiment will explain the pressurized gas mist bathing system further having a means for electrically charging a generated mist. As to the same parts as those of the first embodiment shown in FIG. 1, the same numerals will be given, and detailed explanation will be omitted.

As shown in FIG. 13, the pressurized gas mist bathing system of this embodiment is arranged with an electrode 22 in the vicinity of an exit of a gas mist outlet 33 of the gas mist generator 30. The electrode 22 is connected to a power supply device 21, and the control device 60 sets voltage values and performs on-off control.

The electrode 22 supplies an electric charge (minus charge is desirable) when exhausting the mist generated by the gas mist generator 30. Thereby, the mist is made a charged condition, so that adhesion to a charged material can be heightened. That is, if heightening adhesion to the skin and the mucous membrane of the living body, an effect of more increasing absorption rate of gas by the pressurized gas mist bathing is further heightened, and if the gas mist contains the above mentioned medicines, penetration into the skin and the mucous membrane can be accelerated similarly.

For carrying out the pressurized gas mist bathing by using the pressurized gas mist bathing system of the present embodiment, at first, the sealed g liquid storage 34 is opened, and the generator main body 31 and the liquid supply pipe 41 are set to accomplish the gas mist generator 30. The pressure cover 50 is fixedly secured to the living body (herein, the lower extremity) and closed.

Subsequently, supply of gas starts from the gas supply means 10 to the gas mist generator 30. During this period, the control device 60 controls supply pressure of gas, temperature and others. Further, the control device 60 turns on the power supply device 21 and gives an electric charge to the mist from the electrode 22.

The generated gas mist is discharged from the gas mist outlet 33 into the pressure cover 50 through the gas mist supply pipe 43. The control device 60 controls each of the means from measuring values of the manometer 71 and the temperature gauge 72 placed within the pressure cover 50 such that the inside of the pressure cover 50 becomes the optimum pressurized and heated conditions (around 1.02 to 2.5 air pressure and around 38° C.), and under these conditions, the pressurized gas mist bathing is carried out.

Having composed the structure as mentioned above, according to the pressurized gas mist bathing system, in the gas mist generating means, the liquid storage is made displaceable with another liquid storage, whereby attention is given to hygiene as well as cost reduction is realized.

The above references have explained the embodiments of the invention, but are not limited thereto, and so far as not deviating from the subject matter of the invention, various kinds of embodiments are, of course, available.

INDUSTRIAL APPLICABILITY

The present invention relates to the pressurized gas mist bathing system for improving absorption efficiency of gas from the skin or the mucous membrane of the living body, in which the mist is prepared by pulverizing and dissolving the liquid of oxygen or carbon dioxide and the medicines or the mixed gas of oxygen and carbon dioxide and the medicines, and the mist is caused to directly contact the skin and mucous membrane of the living body at pressure of not less than a predetermined value accompanying industrial applicability.

EXPLANATION OF THE REFERENCE NUMERALS

10: gas supply means
21: power supply device
22: electrode
30: gas mist generator
30A: space
31: generator main body
31A, 31B: plates
32: fluid nozzle
32A: gas supply part
32B: liquid supply part
33: gas mist outlet
34: liquid storage
34A: connection part
35: liquid outlet
41: liquid supply pipe
42: liquid pressurizer
43: gas mist supply pipe
44: cornice shaped pipe
50, 50A, 50B, 50C, 50D, 50E, 80, 80A, 80B, 80C, 80D: pressure cover
51, 51A, 51B, 51C, 51D, 51E, 81, 81A, 81B, 81C, 81D: supply port
52, 52A, 52B, 52C, 52D, 52E, 52F, 53A, 82, 82A, 82B, 82C, 82D: stopper
53F, 83D: fixing part
54F, 84D: cover part
60: control device
71: manometer
72: temperature gauge
90, 90A, 90B, 90C, 90D: pressurizing means
91, 91A, 91B, 91C, 91D: gas storage
92, 92A, 92B, 92C, 92D: supply port

The invention claimed is:

1. A pressurized gas mist bathing system, which causes a gas mist to contact a skin or a mucous membrane of a living body in a high pressure not less than a predetermined value, the gas mist being prepared by pulverizing liquid and the gas mist of micron size dissolving oxygen and/or carbon dioxide gases, comprising:

a gas supply device;

a gas mist generator connected to the gas supply device, and having a generator main body including a fluid nozzle for generating the gas mist and a gas mist outlet for discharging the gas mist in an upper part of the generator main body, the fluid nozzle having a gas supply part and a liquid supply part, and a liquid storage for storing the liquid, displaceably and replaceably connected to the generator main body and including a liquid outlet disposed on a bottom part of the liquid storage and a connecting part on a top part of the liquid storage, the liquid storage being connected to the generator main body in a lower part of the generator main body at the connecting part;

a pressure cover connected to the gas mist outlet to supply the gas mist therein, the pressure cover for covering the skin or the mucous membrane of the living body and formed with a space for sealing inside the gas mist supplied from the gas mist outlet; and a liquid supply pipe, disposed outside of the generator main body and detachable from the liquid storage, wherein the liquid supply part is connected to the liquid outlet through the liquid supply pipe and circulates the liquid in the liquid supply pipe, and the connecting part and the liquid outlet are sealed with a plug or a film and the liquid is stored in the liquid storage before the liquid storage is connected to the generator main body so that, in the gas mist generator, at least the liquid storage is displaceable and replaceable with another liquid storage.

2. The pressurized gas mist bathing system, according to claim 1, further comprising sensors for detecting measured values of air pressure, temperature, concentration of oxygen and concentration of carbon dioxide, and moisture, and a control device for controlling an interior of the pressure cover based on the measured values of the sensors to be within ranges of set values previously determined.

3. The pressurized gas mist bathing system, according to claim 2, wherein the gas mist is configured to be supplied intermittently into the pressure cover by the control device, so that the pressure cover is effected with interval pressurization.

4. The pressurized gas mist bathing system, according to claim 2, wherein the control device holds pressure at 1.02 to 2.5 atmospheric pressure within the pressure cover during pressurized gas mist bathing.

5. The pressurized gas mist bathing system, according to claim 2, wherein the control device is configured to stop gas supply from the gas supply device when the pressure value becomes more than the predetermined value.

6. The pressurized gas mist bathing system, according to claim 1, wherein the liquid supply pipe includes a liquid pressurizer.

7. The pressurized gas mist bathing system, according to claim 6, wherein the liquid pressurizer is disposed between the liquid supply part and the liquid outlet.

8. The pressurized gas mist bathing system, according to claim 1, further comprising a pressurizing device for pressurizing an interior of the pressure cover.

9. The pressurized gas mist bathing system, according to claim 8, wherein the pressurizing device communicates with the pressure cover, and has a hollow gas storage to discharge the gas mist into the pressure cover.

10. The pressurized gas mist bathing system, according to claim 9, wherein the pressurizing device is configured to intermittently discharge the gas mist into the pressure cover, so that interval pressurization is carried out on the pressure cover.

11. The pressurized gas mist bathing system, according to claim 1, wherein the liquid is any one or plural combination of water, ionic water, ozone water, physiological salt solution, purified water, or sterilized and purified water.

12. The pressurized gas mist bathing system, according to claim 11, wherein the liquid further contains any one or plural combination of menthol, vitamin E, vitamin C derivative, retinol, anesthetic agent, cyclodextrin, photo catalyst, complex of photo catalyst and apatite, hyaluronic acid, coenzyme Q10, seed oil, propolith, ethanol, chlorhexidine gluconate, amphoteric surface active agent, benzalkonium chloride, alkyl diamino etherglycine acetate, sodium hypochlorite, peracetic acid, sodium sesquicarbonate, silica, povidone-iodine, sodium hydrogen carbonate, carbonate spring agent of high concentration, anti-allergic agent, anti-inflammatory agent, anti-febrile agent, anti-fungus agent, anti-influenza virus agent, influenza vaccine, steroid agent, anti-cancer agent, anti-hypertensive agent, cosmetic, or trichogen.

13. The pressurized gas mist bathing system, according to claim 1, wherein a size of the gas mist supplied from the gas mist generator into the pressure cover is not larger than 10 μm.

14. The pressurized gas mist bathing system, according to claim 1, further comprising an electric charge giving device for giving a charge to the gas mist supplied by the gas mist generator.

15. The pressurized gas mist bathing system, according to claim 14, wherein the charge is minus.

16. The pressurized gas mist bathing system, according to claim 1, wherein the gas mist generator has a gas mist supply pipe for supplying the gas mist into the pressure cover, and at least one part of the gas mist supply pipe includes a pipe formed into a bellows.

17. The pressurized gas mist bathing system, according to claim 1, wherein the gas mist generator has a gas mist supply pipe for supplying the gas mist into the pressure cover, and the gas mist supply pipe includes a check valve.

18. The pressurized gas mist bathing system, according to claim 1, wherein the generator main body is sterile before the liquid storage is connected to the generator main body.

19. The pressurized gas mist bathing system, according to claim 1, wherein the gas mist generator includes one or plural sheets of plates having inside fine pores for finely dividing the gas mists.

20. The pressurized gas mist bathing system, according to claim 1, wherein the generator main body includes an upper plate and a lower plate, arranged apart from each other therein and having inside fine pores for finely dividing the gas mists, each of the inside fine pores of the upper plate having a diameter larger than that of the lower plate.

* * * * *